(12) United States Patent
Baranyai

(10) Patent No.: US 9,751,829 B2
(45) Date of Patent: Sep. 5, 2017

(54) METHOD FOR PRODUCING A CRYSTALLINE SOLID FROM GLYCINE-N,N-DIACETIC ACID DERIVATIVES WITH SUFFICIENTLY REDUCED HYGROSCOPICITY

(71) Applicant: BASF SE, Ludwigshafen (DE)

(72) Inventor: Andreas Baranyai, Heitersheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/096,678

(22) Filed: Apr. 12, 2016

(65) Prior Publication Data

US 2016/0221930 A1 Aug. 4, 2016

Related U.S. Application Data

(63) Continuation of application No. 13/391,397, filed as application No. PCT/EP2010/005219 on Aug. 25, 2010, now Pat. No. 9,376,649.

(30) Foreign Application Priority Data

Aug. 26, 2009 (DE) .................. 10 2009 038 951

(51) Int. Cl.
| | | |
|---|---|---|
| C11D 3/33 | (2006.01) |
| C07C 229/16 | (2006.01) |
| C07C 229/76 | (2006.01) |
| C07C 227/42 | (2006.01) |
| C11D 7/32 | (2006.01) |

(52) U.S. Cl.
CPC .......... *C07C 229/16* (2013.01); *C07C 227/42* (2013.01); *C11D 3/33* (2013.01); *C11D 7/3245* (2013.01); *C07B 2200/13* (2013.01)

(58) Field of Classification Search
CPC ....... C07C 229/16; C07C 227/42; C11D 3/33; C11D 7/3245; C07B 2200/13
See application file for complete search history.

(56) References Cited

U.S. PATENT DOCUMENTS

| | | |
|---|---|---|
| 3,932,316 A | 1/1976 | Sagel et al. |
| 5,786,313 A | 7/1998 | Schneider et al. |
| 5,932,015 A | 8/1999 | Yoneda et al. |
| 5,981,798 A | 11/1999 | Schonherr et al. |
| 9,376,649 B2 * | 6/2016 | Baranyai ............... C07C 227/42 |
| 9,540,597 B2 * | 1/2017 | Mrzena .................. C11D 3/33 |
| 2010/0056817 A1 | 3/2010 | Meunier et al. |
| 2011/0054215 A1 | 3/2011 | Euser et al. |
| 2012/0046491 A1 | 2/2012 | Mrzena et al. |
| 2014/0073554 A1 * | 3/2014 | Van Der Eerden ...... C11D 3/08 510/533 |

FOREIGN PATENT DOCUMENTS

| | | | |
|---|---|---|---|
| DE | 196 49 681 | 6/1998 | |
| DE | WO 2010133618 A1 * | 11/2010 | ........... C07C 229/24 |
| EP | 2 161 075 | 3/2010 | |
| JP | 62-126118 | 6/1987 | |
| WO | 94 29421 | 12/1994 | |
| WO | 2009 103822 | 8/2009 | |
| WO | WO 2009103822 | * 8/2009 | |

OTHER PUBLICATIONS

International Search Report issued on Mar. 23, 2011 in PCT/EP10/005219 filed on Aug. 25, 2010.
Notice of Opposition as received in the corresponding European patent EP 2 470 496 dated Sep. 30, 2016.
Ullmann Encyclopedia—Fertilizers Granulation, 2009, pp. 253-277.
H. Groenewald, "Die jeweiligen Staerken nutzen", Chjemie Technik Mar. 2006, pp. 44-46.
Technical Information, TI/EVD 1418, (May 2007) Seite 1, Von 14, "A. Trilon® M Types", 16 pages.

* cited by examiner

*Primary Examiner* — Michael Barker
*Assistant Examiner* — Amanda L Aguirre
(74) *Attorney, Agent, or Firm* — Oblon, McClelland, Maier & Neustadt, L.L.P.

(57) ABSTRACT

The present invention relates to a process for preparing a crystalline solid from glycine-N,N-diacetic acid derivatives (e.g., MGDA) of sufficiently low hygroscopicity, which is characterized in that at least one crystalline compound of the formula I is introduced as seed, and a spray granulation is carried out with at least one compound of the formula I, preferably followed by a heat treatment.

16 Claims, No Drawings

METHOD FOR PRODUCING A CRYSTALLINE SOLID FROM GLYCINE-N,N-DIACETIC ACID DERIVATIVES WITH SUFFICIENTLY REDUCED HYGROSCOPICITY

This application is a continuation of U.S. application Ser. No. 13/391,397 filed Feb. 23, 2012, now U.S. Pat. No. 9,376,649, and incorporated herein by reference, which is a National Stage of PCT/EP10/05219 filed Aug. 25, 2010 and claims the benefit of DE 10 2009 038 951.2 filed Aug. 26, 2009.

Complexing agents for alkaline earth metal ions and heavy metal ions, of the kind used in detergents, for example, are typically synthesized in aqueous solution. For certain applications they are required in solid form.

Typical processes for producing solids from solutions are, in particular, crystallization processes and spray drying processes. It is known that crystalline solid of the kind produced, for example, in evaporative or cooling crystallization processes may contain water of crystallization and under ambient conditions is usually less hygroscopic and more storage-stable than amorphous solid. Through spray drying processes (e.g., in a spraying tower or in a fluidized spraying bed), in contrast, the solid is obtained in amorphous form. In this form the solid is often highly hygroscopic and when stored in the open under ambient conditions it loses its capacity for free flow within a short time. In the literature, therefore, measures are described for increasing the storage-stability of sprayed powders, an example being the compacting or aftertreatment of builders for laundry detergents with benzoic acid in U.S. Pat. No. 3,932,316.

Glycine-N,N-diacetic acid derivatives as complexing agents for alkaline earth metal ions and heavy metal ions in a wide variety of industrial application fields are known from WO 94/29421. These glycine-N,N-diacetic acid derivatives, an example being α-alanine-N,N-diacetic acid (MGDA) in the form of the trisodium salt, are highly inhibited in their crystallization, and so typical crystallization processes are impossible or uneconomic. The aftertreatment of amorphous sprayed powders of these compounds with additives, as for example benzoic acid in accordance with U.S. Pat. No. 3,932,316, is undesirable for certain applications, and may also only improve the storage-stability to a limited extent. The stability of a crystalline solid is not attained.

It was an object of the present invention, therefore, to provide a virtually nonhygroscopic, stable, preferably crystalline solid substantially comprising glycine-N,N-diacetic acid derivatives which is largely free from additives.

The present invention relates to a process for preparing a preferably crystalline solid preferably having, for processing and application, for example, a sufficiently low hygroscopicity and substantially comprising glycine-N,N-diacetic acid derivatives of the general formula I

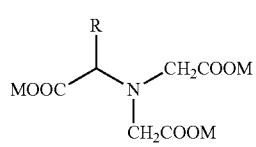 (I)

in which
R is $C_1$ to $C_{30}$ alkyl or $C_2$ to $C_{30}$ alkenyl, which may additionally carry as substituents up to 5 hydroxyl groups, formyl groups, $C_1$ to $C_4$ alkoxy groups, phenoxy groups or $C_1$ to $C_4$ alkoxycarbonyl groups and may be interrupted by up to 5 nonadjacent oxygen atoms, alkoxylate moieties of the formula

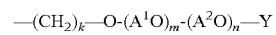

in which $A^1$ and $A^2$ independently of one another denote 1,2-alkylene groups having 2 to 4 C atoms, Y is hydrogen, $C_1$ to $C_{12}$ alkyl, phenyl or $C_1$ to $C_4$ alkoxycarbonyl, and k is the number 1, 2 or 3, and also m and n are each numbers from 0 to 50, the sum of m+n necessarily being at least 4, phenylalkyl groups having 1 to 20 C atoms in the alkyl, a five- or six-membered, unsaturated or saturated, heterocyclic ring having up to three heteroatoms from the group consisting of nitrogen, oxygen, and sulfur, which may additionally be benzofused, it being possible for all phenyl rings and heterocyclic rings in the definitions for R additionally to carry as substituents up to three $C_1$ to $C_4$ alkyl groups, hydroxyl groups, carboxyl groups, sulfo groups or $C_1$ to $C_4$ alkoxycarbonyl groups, or is a radical of the formula

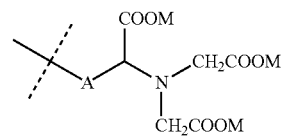

where A denotes a $C_1$ to $C_{12}$ alkylene bridge or a chemical bond, and
each M independently of any other is hydrogen, alkali metal, alkaline earth metal, ammonium or substituted ammonium (e.g., organic amine salts) in the corresponding stoichiometric amounts,
which is characterized in that at least one crystalline compound of the formula I is introduced as seed, and a spray granulation (preferably in a granulator) is carried out with at least one compound of the formula I.

Particularly preferred compounds of the formula I are those as described in DE 196 49 681.

In an inherently typical way, in a spray granulation, small to ultra small droplets in the region of 50 μm of a liquid sprayed through nozzles are dried in a reaction chamber, by direct heat transfer in a warm or hot air stream to form particles. From aqueous solutions, emulsions or dispersions, for example, ultra small particles (seeds) are first produced in the reaction chamber through drying of these sprayed droplets (alternatively, these seeds may also be introduced at the start). These seeds are held in a state of suspension (fluidization) in a fluidized bed, and form the surface for layerwise adsorption and drying of further sprayed droplets. The particles thus produced can be removed continuously from the drying chamber without interruption to the drying procedure by means of a classifying discharge in a flexible way—for example, with freely adjustable particle sizes. On the process of spray granulation, see also H. Uhlemann, L. Mörl, "Wirbelschicht—Sprühgranulation" Springer-Verlag 2000 (ISBN 3-540-66985-X).

The process of the present invention is characterized in that at least one preferably crystalline compound of the formula I is introduced in the form of seeds and then in an inherently typical way a spray granulation is carried out with at least one compound of the formula I, preferably in solution (more particularly in aqueous solution, e.g., about 40% strength).

A spray granulation is carried out preferably with the following parameters:

Preferred air feed temperature: 90-160° C., preferred air departure temperature: 40-110° C., preferred product temperature: 40-110° C., preferred spraying air temperature: 70-110° C., preferred spraying air pressure: 1-6 bar, preferred spraying solution temperature: 50-95° C.

In the process of the invention, for example, liquid raw material (e.g., a 40% strength aqueous solution of a compound of the formula I) is sprayed onto the crystal seeds (of compounds of the formula I) in fluid motion in the hot air stream, and thereby dries and causes the seeds to grow. This procedure is preferably operated continuously, with preferably continuous removal of a portion of the product from the granulator, followed by its treatment with an additional tempering step (heat-treatment step). This lowers the hygroscopicity of the product, preferably by raising the crystalline fraction in the product. The product thus treated represents the end product, and in turn preferably a portion is ground and introduced as new seeds back into the granulator.

The product is preferably heat-aftertreated (tempered) with the following temperature profile: beginning with a bed temperature of 50-90° C., the bed temperature is raised to 90-130° C. over the course of about an hour, and then held at this temperature for about 60 minutes.

The granulator is preferably a fluid-bed spray granulator which is equipped, for example, with a cyclone and/or a filter.

With the process of the present invention, it is necessary preferably only right at the beginning to introduce crystalline product, after which a spray granulation (which without introduction of crystalline product would only produce far more amorphous granules, for example) and the subsequent tempering (heat-treatment) results persistently in a product having a relatively high crystalline fraction (and, consequently, substantially lower hygroscopicity).

The expression "crystalline" relates preferably to a crystalline fraction of at least 60% by weight.

A solid is said here to be nonhygroscopic or of sufficiently low hygroscopicity when on storage in the open under normal ambient conditions, e.g., 25° C. and a relative humidity of 76%, it preserves its consistency as (preferably free-flowing) powder or granules over a period of at least one day, preferably one week.

The preferably crystalline solid prepared in accordance with the invention substantially comprises compounds of the formula I, and small amounts of starting products and/or by-products from the preparation of the glycine-N,N-diacetic acid derivatives I may additionally be present. Typical purities for the compounds I, depending on the synthesis process employed, are 70% to 99.9% by weight, more particularly 80% to 99.5% by weight, based in each case on the solids content.

The crystalline starting substance may be prepared, for example, by the process described in DE 196 49 681.

The process of the invention is suitable preferably for those compounds I in which R is $C_1$ to $C_{20}$ alkyl, $C_2$ to $C_{20}$ alkenyl or a radical of the formula

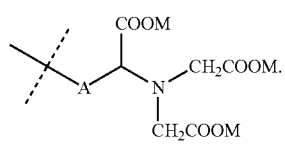

As compound I it is particularly preferred to use α-alanine-N,N-diacetic acid (R=$CH_3$, MGDA) and its salts. It is preferred, for example, to use its alkali metal salts, ammonium salts, and substituted ammonium salts.

Suitable such salts are in particular the sodium, potassium, and ammonium salts, more particularly the trisodium, tripotassium, and triammonium salt, and also organic triamine salts with a tertiary nitrogen atom.

Suitable bases as a parent to the organic amine salts are, in particular, tertiary amines, such as trialkylamines having 1 to 4 C atoms in the alkyl, such as trimethylamine and triethylamine, and trialkanolamines having 2 or 3 C atoms in the alkanol residue, preferably triethanolamine, tri-n-propanolamine or triisopropanolamine.

The calcium salts and magnesium salts are used in particular as alkaline earth metal salts.

Besides methyl, straight-chain or branched alk(en)yl radicals contemplated for the radical R include in particular $C_2$ to $C_{17}$ alkyl and alkenyl, more particularly straight-chain radicals derived from saturated or unsaturated fatty acids.

Examples of individual radicals R are as follows: ethyl, n-propyl, isopropyl, n-butyl, isobutyl, sec-butyl, tert-butyl, n-pentyl, isopentyl, tert-pentyl, neopentyl, n-hexyl, n-heptyl, 3-heptyl (derived from 2-ethylhexanoic acid), n-octyl, isooctyl (derived from isononanoic acid), n-nonyl, n-decyl, n-undecyl, n-dodecyl, isododecyl (derived from isotridecanoic acid), n-tridecyl, n-tetradecyl, n-pentadecyl, n-hexadecyl, n-heptadecyl, n-octadecyl, n-nonadecyl, n-eicosyl and n-heptadecenyl (derived from oleic acid). For R it is also possible for mixtures to occur, more particularly those which derive from naturally occurring fatty acids and from synthetically produced technical acids, as a result of oxo-process synthesis, for example.

Serving as $C_1$ to $C_{12}$ alkylene bridges A are, in particular, polymethylene moieties of the formula $(CH_2)_k$, in which k denotes a number from 2 to 12, more particularly from 2 to 8, i.e., 1,2-ethylene, 1,3-propylene, 1,4-butylene, pentamethylene, hexamethylene, heptamethylene, octamethylene, nonamethylene, decamethylene, undecamethylene and dodecamethylene. Hexamethylene, octamethylene, 1,2-ethylene and 1,4-butylene are particularly preferred in this context. In addition, however, branched $C_1$ to $C_{12}$ alkylene groups may also occur, e.g., —$CH_2CH(CH_3)CH_2$—, —$CH_2C(CH_3)_2CH_2$—, —$CH_2CH(C_2H_5)$—, or $CH_2CH(CH_3)$—.

The $C_1$ to $C_{30}$ alkyl and $C_2$ to $C_{30}$ alkenyl groups may carry up to 5, more particularly up to 3, additional substituents of the stated type, and may be interrupted by up to 5, more particularly up to 3, nonadjacent oxygen atoms. Examples of such substituted alk(en)yl groups are —$CH_2OH$, —$CH_2CH_2OH$, —$CH_2CH_2$—O—$CH_3$, —$CH_2CH_2$—O—$CH_2CH_2$—O—$CH_3$, —$CH_2$—O—$CH_2CH_3$, —$CH_2$—O—$CH_2CH_2$—OH, —$CH_2$—CHO, —$CH_2$—OPh, —$CH_2$—$COOCH_3$ or —$CH_2CH_2$—$COOCH_3$.

Alkoxylate moieties contemplated include in particular those in which m and n are each independently of one another numbers from 0 to 30, especially from 0 to 15. $A^1$ and $A^2$ preferably denote groups derived from butylene oxide and especially groups derived from propylene oxide and from ethylene oxide. Of particular interest are pure ethoxylates and pure propoxylates, although ethylene oxide-propylene oxide block structures may also occur.

As five- or six-membered, unsaturated or saturated, heterocyclic rings having up to three heteroatoms from the group consisting of nitrogen, oxygen, and sulfur, which may additionally be benzofused and may be substituted by the designated radicals, the following are contemplated: tetrahydrofuran, furan, tetrahydrothiophene, thiophene, 2,5-dimethylthiophene, pyrrolidine, pyrroline, pyrrole, isoxazole, oxazole, thiazole, pyrazole, imidazoline, imidazole, 1,2,3-triazolidine, 1,2,3- and 1,2,4-triazole, 1,2,3-, 1,2,4- and 1,2,5-oxadiazole, tetrahydropyran, dihydropyran, 2H- and 4H-pyran, piperidine, 1,3- and 1,4-dioxane, morpholine, pyrazan, pyridine, α-, β- and γ-picoline, α- and γ-piperidone, pyrimidine, pyridazine, pyrazine, 1,2,5-oxathiazine, 1,3,5-, 1,2,3- and 1,2,4-triazine, benzofuran, thionaphthene, indoline, indole, isoindoline, benzoxazole, indazole, benzimidazole, chroman, isochroman, 2H- and 4H-chromene, quinoline, isoquinoline, 1,2,3,4-tetrahydroisoquinoline, cinnoline, quinazoline, quinoxaline, phthalazine, and benzo-1,2,3-triazine.

N—H moieties in the stated heterocyclic rings ought as far as possible to be in derivatized form, for instance as an N-alkyl moiety.

In the case of substitution on the phenyl rings or the heterocyclic rings, there are preferably two (identical or different) or, more particularly, one individual substituent present.

Examples of optionally substituted phenylalkyl groups and alkyl groups which carry heterocyclic rings, for R, are benzyl, 2-phenylethyl, 3-phenylpropyl, 4-phenylbutyl, o-, m- or p-hydroxybenzyl, o-, m- or p-carboxybenzyl, o-, m- or p-sulfobenzyl, o-, m- or p-methoxy- or -ethoxycarbonylbenzyl, 2-furylmethyl, N-methylpiperidin-4-ylmethyl or 2-, 3- or 4-pyridinylmethyl.

In the case of substitution on phenyl rings and also on heterocyclic rings, the groups in question are preferably groups conferring solubility in water, such as hydroxyl groups, carboxyl groups or sulfo groups.

The radicals listed above for R should also be understood correspondingly, to be examples of the stated $C_1$ to $C_4$, $C_1$ to $C_{12}$, and $C_1$ to $C_{20}$ alkyl groups.

The crystalline solid prepared in accordance with the invention is especially suitable as a component for solid detergent formulations. In addition, therefore, solid detergent formulations which comprise the crystalline solid of sufficiently low hygroscopicity, prepared in accordance with the invention, comprising glycine-N,N-diacetic acid derivatives I, as complexing agent for alkaline earth metal ions and heavy metal ions, in the amounts customary for this purpose, in addition to other customary ingredients of such formulations, are also provided by the present invention. Compositions and customary ingredients of solid detergent formulations of this kind are known to the skilled person and therefore need not be elucidated in any more detail here.

The example below is intended to elucidate the invention in more detail. The glycine-N,N-diacetic acid derivative I used was α-alanine-N,N-diacetic acid (methylglycine-N,N-diacetic acid, "MGDA"), trisodium salt.

EXAMPLE

The procedure below was carried out in a fluid-bed spray granulator which is equipped with a cyclone, a filter, and a gas scrubber.

The starting material (Trilon® M, liquid, from BASF AG) was heated to 90° C. with continuous and intense mixing and was used at this temperature for the granulation. Under the following conditions, a stable granulating operation was achieved:

| Process parameters: | |
| --- | --- |
| Feed air temperature | 125° C. |
| Departing air temperature | 65° C. |
| Product temperature | 65-70° C. |
| Intake air volume | 1300 m³/h |
| Spraying air temperature | 90° C. |
| Spraying air pressure | 3 bar |
| Spraying solution temperature | 80° C. |

In order to raise the crystallinity, the product prepared was aftertreated with a temperature profile commencing with a bed temperature of 70° C., then raising this temperature to around 110-120° C. over the course of around an hour, and subsequently holding at this temperature for around 60 minutes.

Screening at 1000 microns and re-use of the ground coarse material as crystallization seeds for the granulation process led to a stable operation with a yield of about 20 kg of granules per hour in the desired quality. The introduction of comminuted material was advantageous for the process, in order to maintain the height of the bed, and in order to obtain the product in a crystalline form.

The invention claimed is:

1. A process for preparing a crystalline solid, the process comprising spray granulating an aqueous solution of a liquid raw material on a crystalline seed material to obtain the crystalline solid,
wherein the crystalline seed material, the liquid raw material, and the crystalline solid each comprise a glycine-N,N-diacetic acid derivative of formula (I)

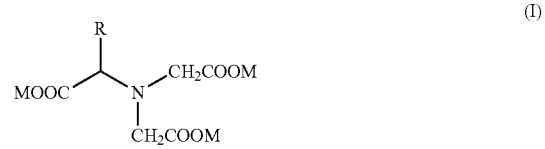

wherein R is:
a $C_1$ to $C_{30}$ alkyl or a $C_2$ to $C_{30}$ alkenyl, optionally having up to 5 substituents selected from a hydroxyl group, a formyl group, a $C_1$ to $C_4$ alkoxy group, a phenoxy group and a $C_1$ to $C_4$ alkoxycarbonyl group and optionally having up to 5 nonadjacent oxygen atoms;
an alkoxylate moiety of formula (II)

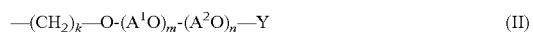

in which $A^1$ and $A^2$ each independently are alkylene groups having 2 to 4 C atoms, Y is hydrogen, $C_1$ to $C_{12}$ alkyl, phenyl or $C_1$ to $C_4$ alkoxycarbonyl, k is 1, 2 or 3, and m and n are each integers of 0 to 50, a sum of m+n being at least 4;
a phenylalkyl group having 1 to 20 C atoms in an alkyl part of the group;
a five- or six-membered, unsaturated or saturated, heterocyclic ring having up to three heteroatoms from the group consisting of nitrogen, oxygen, and sulfur, which may additionally be benzofused, it being possible for any phenyl ring and heterocyclic ring of R additionally to have up to three substituents selected from the group consisting of a $C_1$ to $C_4$ alkyl group, a hydroxyl group, a carboxyl group, a sulfo group and a $C_1$ to $C_4$ alkoxycarbonyl group; or R is a radical of formula (III)

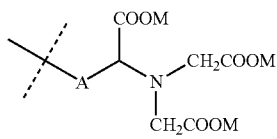 (III)

where A is a $C_1$ to $C_{12}$ alkylene bridge or a chemical bond, and each M independently is hydrogen, an alkali metal, an alkaline earth metal, ammonium or substituted ammonium in a corresponding stoichiometric amount.

2. The process according to claim 1, wherein the process is performed in a granulator and the process further comprises removing a part of the crystalline solid from the granulator, grinding the crystalline solid to obtain additional crystalline seed material, and introducing the additional crystalline seed material into the granulator.

3. The process according to claim 1, wherein R is $C_1$ to $C_{20}$ alkyl, $C_2$ to $C_{20}$ alkenyl or a radical of formula (III)

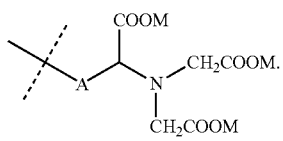 (III)

4. The process according to claim 1, wherein the glycine-N,N-diacetic acid derivative is α-alanine-N,N-diacetic acid (MGDA) or an alkali metal salt, an ammonium salt or a substituted amine salt thereof.

5. The process of claim 1, wherein R is $C_1$ to $C_{20}$ alkyl.

6. The process of claim 1, wherein R is $C_2$ to $C_{20}$ alkenyl.

7. The process of claim 1, wherein R is an alkoxylate moiety of formula (II)

$$-(CH_2)_k-O-(A^1O)_m-(A^2O)_n-Y \qquad (II).$$

8. The process of claim 1, wherein R is a radical of formula (III)

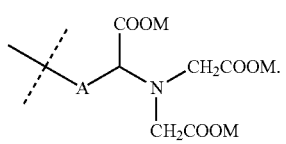 (III)

9. The process of claim 1, wherein A is hexamethylene, octamethylene, 1,2-ethylene, or 1,4-butylene.

10. The process of claim 1, wherein the spray granulating comprises an air feed temperature is 90-160° C.

11. The process of claim 1, wherein the spray granulating comprises an air departure temperature is 40-110° C.

12. The process of claim 1, wherein the crystalline solid temperature obtained by the spray granulating is 40-110° C.

13. The process of claim 1, wherein the spray granulating comprises a spraying air temperature is 70-110° C.

14. The process of claim 1, wherein the spray granulating comprises a spraying air pressure is 1-6 bar.

15. The process of claim 1, wherein the liquid raw material is at a temperature is 50-95° C.

16. The process of claim 1, wherein the obtained crystalline solid preserves its consistency as a powder or granules over a period of at least one day when stored at 25° C. and a relative humidity of 76%.

* * * * *